United States Patent
Savitzky et al.

(10) Patent No.: US 6,994,994 B1
(45) Date of Patent: Feb. 7, 2006

(54) SPLICE VARIANTS OF CD40-RECEPTOR

(75) Inventors: Kinneret Savitzky, Tel Aviv (IL); Rami Khosravi, Herzilya (IL); Menashe Elazar, Mevaseret Zion (IL)

(73) Assignee: Compugent LTD, Tel Aviv (IL)

( * ) Notice: Subject to any disclaimer, the term of this patent is extended or adjusted under 35 U.S.C. 154(b) by 289 days.

(21) Appl. No.: 10/031,607

(22) PCT Filed: Jul. 19, 2000

(86) PCT No.: PCT/IL00/00427

§ 371 (c)(1),
(2), (4) Date: Jun. 12, 2002

(87) PCT Pub. No.: WO01/05967

PCT Pub. Date: Jan. 25, 2001

(30) Foreign Application Priority Data

Jul. 20, 1999 (IL) ..................................... 130989

(51) Int. Cl.
C12N 15/12 (2006.01)
C12N 5/10 (2006.01)
C12P 21/02 (2006.01)
C07K 14/47 (2006.01)

(52) U.S. Cl. .................. 435/69.1; 435/71.1; 435/320.1; 435/325; 435/471; 530/350

(58) Field of Classification Search ................. 530/350; 435/69.1, 71.1, 320.1
See application file for complete search history.

(56) References Cited

U.S. PATENT DOCUMENTS 6,376,459 B1 * 4/2002 Aruffo et al. ................. 514/2

FOREIGN PATENT DOCUMENTS

| EP | 0555880 A2 | 8/1993 |
|---|---|---|
| WO | WO 9723614 A1 | 7/1997 |
| WO | WO 9853842 A1 | 12/1998 |

OTHER PUBLICATIONS

Database PIR; Accession No.: A60771, Stamenkovic et al, 1989.*
Database EMEST 'Online! EMBL; ID HS884118; AC R49884, (May 24, 1995): Hillier I. et al.: "CD40L receptor precursor" XP002155584 EST nucleotide sequence.
Database EMEST 'Online! EMBL; ID A1784157; AC A1784157, (Jul. 2, 1999) National Cancer Institute, Cancer Genom Anatomy Project (CGAP): "CD40L receptor precursor" XP002155585 EST nucleotide sequence.
Database EMEST 'Online! EMBL; ID HSH94398; AC H4398. (Dec. 6, 1995): Hillier L et al.: CD40L, recepto precursor XP002155586 EST nucleotide sequence.
Database GCG_GENESQ:D 'Online! GCG; ID V64740; AC V64740, (Jan. 29, 1999); Capon D et al.: "Human immunodefiency virus" XP002155587 HIV anti-viral oligonucleotide primer.
Database EMEST 'Online! EMBL; ID MMA60117; AC AA060117, (Sep. 24, 1996); Marra M et al.: Mouse murine CD40 mRNA XP002155588 EST nucleotide sequence.
van Kooten et al., Frontiers in Bioscience 1, pp. 1-11 (Jan. 1, 1997).

* cited by examiner

Primary Examiner—Janet Andres
Assistant Examiner—Fozia Hamud
(74) Attorney, Agent, or Firm—Ivor R. Elrifi; David E. Johnson; Mintz Levin

(57) ABSTRACT

The present invention concerns six novel variants of alternative splicing of the CD40 receptor.

2 Claims, 12 Drawing Sheets

```
                        1                                                    50
        mCD40Alt19   MVSLPRLCAL WGCLLTAVHL GQCVTCSDKQ YLHDGQCCDL CQPGSRLTSH
         mCD40Alt8   MVSLPRLCAL WGCLLTAVHL GQCVTCSDKQ YLHDGQCCDL CQPGSRLTSH
   mCD40Alt6Corected  MVSLPRLCAL WGCLLTAVHL GQCVTCSDKQ YLHDGQCCDL CQPGSRLTSH
           mCD40-wt   MVSLPRLCAL WGCLLTAVHL GQCVTCSDKQ YLHDGQCCDL CQPGSRLTSH
       mcd40-pFB1-1-5 MVSLPRLCAL WGCLLTAVHL GQCVTCSDKQ YLHDGQCCDL CQPGSRLTSH 51                                                   100
        mCD40Alt19   CTALEKTQCH PCDSGEFSAQ WNREIRCHQH RHCEP..... ...NQGLRVK
         mCD40Alt8   CTALEKTQCH PCDSGEFSAQ WNREIRCHQH RHCEP..... ...NQGLRVK
   mCD40Alt6Corected  CTALEKTQCH PCDSGEFSAQ WNREIRCHQH RHCEPSAWGC LGRDQGLRVK
           mCD40-wt   CTALEKTQCH PCDSGEFSAQ WNREIRCHQH RHCEP..... ...NQGLRVK
       mcd40-pFB1-1-5 CTALEKTQCH PCDSGEFSAQ WNREIRCHQH RHCEP..... ...NQGLRVK 101                                                   150
        mCD40Alt19   KEGTAESDTV CTCKEGQHCT SKDCEACAQH TPCIPGFGVM EMATE.TTDT
         mCD40Alt8   KEGTAESDTV CTCKEGQHCT SKDCEACAQH TPCIPGFGVM EMATE.TTDT
   mCD40Alt6Corected  KEGTAESDTV CTCKEGQHCT SKDCEACAQH TPCIPGFGVM EMATE.TTDT
           mCD40-wt   KEGTAESDTV CTCKEGQHCT SKDCEACAQH TPCIPGFGVM EMATE.TTDT
       mcd40-pFB1-1-5 KEGTAESDTV CTCKEGQHCT SKDCEACAQH TPCIPGFGVM EMAVRIRTWR
```

```
                  1
      mCD40Alt19   MVSLPRLCAL WGCLLTAVHL GQCVTCSDKQ YLHDGQCCDL CQPGSRLTSH
       mCD40Alt8   MVSLPRLCAL WGCLLTAVHL GQCVTCSDKQ YLHDGQCCDL CQPGSRLTSH
 mCD40Alt6Corected MVSLPRLCAL WGCLLTAVHL GQCVTCSDKQ YLHDGQCCDL CQPGSRLTSH
         mCD40-wt  MVSLPRLCAL WGCLLTAVHL GQCVTCSDKQ YLHDGQCCDL CQPGSRLTSH
     mcd40-pFB1-1-5 MVSLPRLCAL WGCLLTAVHL GQCVTCSDKQ YLHDGQCCDL CQPGSRLTSH 51                                                  100
      mCD40Alt19   CTALEKTQCH PCDSGEFSAQ WNREIRCHQH RHCEP...... ...NQGLRVK
       mCD40Alt8   CTALEKTQCH PCDSGEFSAQ WNREIRCHQH RHCEP...... ...NQGLRVK
 mCD40Alt6Corected CTALEKTQCH PCDSGEFSAQ WNREIRCHQH RHCEPSAWGC LGRDQGLRVK
         mCD40-wt  CTALEKTQCH PCDSGEFSAQ WNREIRCHQH RHCEP...... ...NQGLRVK
     mcd40-pFB1-1-5 CTALEKTQCH PCDSGEFSAQ WNREIRCHQH RHCEP...... ...NQGLRVK 101                                                 150
      mCD40Alt19   KEGTAESDTV CTCKEGQHCT SKDCEACAQH TPCIPGFGVM EMATE.TTDT
       mCD40Alt8   KEGTAESDTV CTCKEGQHCT SKDCEACAQH TPCIPGFGVM EMATE.TTDT
 mCD40Alt6Corected KEGTAESDTV CTCKEGQHCT SKDCEACAQH TPCIPGFGVM EMATE.TTDT
         mCD40-wt  KEGTAESDTV CTCKEGQHCT SKDCEACAQH TPCIPGFGVM EMATE.TTDT
     mcd40-pFB1-1-5 KEGTAESDTV CTCKEGQHCT SKDCEACAQH TPCIPGFGVM EMAVRIRTWR
```

Fig. 1

```
                        151                                                         200
      mCD40Alt19         VCHPCPVGFF SNQSSLFEKC YPWTRFKVPD ASPAGHSCRD GHPHHFRGV
       mCD40Alt8         VCHPCPVGFF SNQSSLFEKC YPWTRFKVPD ASPAGHSCRD GHPHHFRGV
mCD40Alt6Corected        VCHPCPVGFF SNQSSLFEKC YPWTRFKVPD ASPAGHSCRD GHPHHFRGV
         mCD40-wt        VCHPCPVGFF SNQSSLFEKC YPWTSCEDKN LEVLQKGTSQ TNVICGLKSR
     mcd40-pFB1-1-5      SYRKERVRLM SSVV~~~~~~ ~~~~~~~~~~ ~~~~~~~~~~ ~~~~~~~~~

201                                                         250
      mCD40Alt19         SLYQ~~~~~~ ~~~~~~~~~~ ~~~~~~~~~~ ~~~~~~~~~~ ~~~~~~~~~~
       mCD40Alt8         SLYQKGGQET KG~~~~~~~~ ~~~~~~~~~~ ~~~~~~~~~~ ~~~~~~~~~~
mCD40Alt6Corected        SLYQKGGQET KG~~~~~~~~ ~~~~~~~~~~ ~~~~~~~~~~ ~~~~~~~~~~
         mCD40-wt        MRALLVIPVV MGILITIFGV FLYIKKVVKK PKDNEMLPPA ARRQDPQEME
     mcd40-pFB1-1-5      ~~~~~~~~~~ ~~~~~~~~~~ ~~~~~~~~~~ ~~~~~~~~~~ ~~~~~~~~~~

251                                                         298
      mCD40Alt19         ~~~~~~~~~~ ~~~~~~~~~~ ~~~~~~~~~~ ~~~~~~~~~~ ~~~~~~~~
       mCD40Alt8         ~~~~~~~~~~ ~~~~~~~~~~ ~~~~~~~~~~ ~~~~~~~~~~ ~~~~~~~~
mCD40Alt6Corected        ~~~~~~~~~~ ~~~~~~~~~~ ~~~~~~~~~~ ~~~~~~~~~~ ~~~~~~~~
         mCD40-wt        DYPGHNTAAP VQETLHGCQP VTQEDGKESR ISVQERQVTD SIALRPLV
     mcd40-pFB1-1-5      ~~~~~~~~~~ ~~~~~~~~~~ ~~~~~~~~~~ ~~~~~~~~~~ ~~~~~~~~
```

Fig. 1 (Cont.)

```
1    ...................................................ATG    3
                                                         |||
1    gcctcgctcgggcgccagtggtcctgcgcctggtctcacctcgccatg       5

4    GTTCGTCTGCCTCTGCAGTGCGTCCTCTGGGCTGCTTGCTGACCGCTGT     53
     ||||||||||||||||||||||||||||||||||||||||||||||||
51   gttcgtctgcctctgcagtgcgtcctctgggctgcttgctgaccgctgt    100

54   CCATCCAGAACCACCCACTGCATGCAGAGAAAAACAGTACCTAATAAACA   103
     ||||||||||||||||||||||||||||||||||||||||||||||||||
101  ccatccagaaccacccactgcatgcagagaaaaacagtacctaataaaca   150

104  GTCAGTGCTGTGTTCTTTGTGCCAGCCAGGACCAGAAACTGGTGAGTGACTGC  153
     ||||||||||||||||||||||||||||||||||||||||||||||||||
151  gtcagtgctgtgttctttgtgccagccaggaccagaaactggtgagtgactgc  200

154  ACAGAGTTCACTGAAACGGAATGCCTTCCTTGCGGTGAAAGCGAATTCCT   203
     ||||||||||||||||||||||||||||||||||||||||||||||||||
201  acagagttcactgaaacggaatgccttccttgcggtgaaagcgaattcct   250

204  AGACACCTGGAACAGAGAGACACACTGCCACCAGCACAAATACTGCGACC   253
     ||||||||||||||||||||||||||||||||||||||||||||||||||
251  agacacctggaacagagagacacactgccaccagcacaaatactgcgacc   300
```

Fig.4

```
254 CCAACCTAGGGCTTCGGGTCCAGCAGAAGGGCACCTCAGAAACAGACACC  303
    ||||||||||||||||||||||||||||||||||||||||||||||||||
301 ccaacctagggcttcgggtccagcagaagggcacctcagaaacagacacc  350

304 ATCTGCACCTGTGAAGAAGGCTGGCACTGTACGAGTGAGGCCTGTGAGAG  353
    ||||||||||||||||||||||||||||||||||||||||||||||||||
351 atctgcacctgtgaagaaggctggcactgtacgagtgaggcctgtgagag  400

354 CTGTGTCCTGCACCGCTCATGCTCGCCCGGCTTTGGGGTCAAGCAGATT.  402
    |||||||||||||||||||||||||||||||||||||||||||||||||
401 ctgtgtcctgcaccgctcatgctcgcccggctttggggtcaagcagattg  450

403 ................................................GCTGTGA  409
                                                    |||||||
501 tccaatgtgtcatctgctttcgaaaaatgtcacccttggacaagctgtga  550

410 GACCAAAGACCTGGTTGTGCAACAGGCAGGCACAAACAAGACTGATGTTG  459
    ||||||||||||||||||||||||||||||||||||||||||||||||||
551 gaccaaagacctggttgtgcaacaggcaggcacaaacaagactgatgttg  600

460 TCTGTGGTCCCCAGGATCGGCTGAGAGCCCTGGTGGTGATCCCCATCATC  509
    ||||||||||||||||||||||||||||||||||||||||||||||||||
601 tctgtggtccccaggatcggctgagagccctggtggtgatccccatcatc  650
```

Fig.4(Cont.)

510 TTCGGGATCCCTGTTTGC............................. 526
    |||||||||||||||||||
651 ttcgggatccctgtttgccatcctcttggtgctggtctttatcaaaaggt 700

Fig.4(Cont.)

```
 64 CCCGGGATGGTTCGTCTGCCTCTGCAGTGCTCCTCTGGGGCTGCTTGCT 113
    |  |  ||||||||||||||||||||||||||||||||||||||||||||
 42 ctcgccatggttcgtctgcctctgcagtgctcctctgggctgcttgct  91

114 GACCGCTGTCCATCCAGAACCACCCACTGCATGCAGAGAAAACAGTACC 163
    ||||||||||||||||||||||||||||||||||||||||||||||||
 92 gaccgctgtccatccagaaccacccactgcatgcagagaaaacagtacc 141

164 TAATAAACAGTCAGTGCTGTTCTTTGTGCCAGCCAGGACAGAAACTGGTG 213
    |||||||||||||||||||||||||||||||||||||||||||||||||
142 taataaacagtcagtgctgttctttgtgccagccaggacagaaactggtg 191

214 AGTGACTGCACAGAGTTCACTGAAACGGAATGCCTTCCTTGCGGTGAAAG 263
    ||||||||||||||||||||||||||||||||||||||||||||||||||
192 agtgactgcacagagttcactgaaacggaatgccttccttgcggtgaaag 241

264 CGAATTCCTAGACACCTGGAACAGAGAGACACACTGCCACCAGCACAAAT 313
    ||||||||||||||||||||||||||||||||||||||||||||||||||
242 cgaattcctagacacctggaacagagagacacactgccaccagcacaaat 291
```

Fig. 5

```
314  ACTGCGACCCCAACCTAGGGCTTCGGGTCCAGCAGAAGGGCACCTCAgAA  363
     ||||||||||||||||||||||||||||||||||||||||||||||||||
292  actgcgaccccaacctagggcttcgggtccagcagaagggcacctcagaa  341

364  ACAGACACCATCTGCACCTGTGAAGAAGGCTGGCACTGTACGAGTGAGGC  413
     ||||||||||||||||||||||||||||||||||||||||||||||||||
342  acagacaccatctgcacctgtgaagaaggctggcactgtacgagtgaggc  391

414  CTGTGAGAGCTGTGTCCTGCACCGCTCATGCTCGCCCCGGCTTTGGGGTCA  463
     ||||||||||||||||||||||||||||||||||||||||||||||||||
392  ctgtgagagctgtgtcctgcaccgctcatgctcgccccggctttggggtca  441

464  AGCAGATTGCT......................................  474
     |||||||||||
442  agcagattgctacaggggtttctgataccatctgcgagccctgcccagtc  491

475  .....TGTGAGACCAAAGACCTGGTTGTGCAACAGGCAGGCACAAACAAGA  520
          ||||||||||||||||||||||||||||||||||||||||||||||
492  aagctgtgagaccaaagacctggttgtgcaacaggcaggcacaaacaaga  541

521  CTGATGTTGTCTGTGGTCCCCAAGATCGGCTGAGAGCCCTGGTGGTGATC  570
     ||||||||||||||||||||||||||||||||||||||||||||||||||
592  ctgatgttgtctgtggtccccaggatcggctgagagccctggtggtgatc  641
```

Fig. 5 (Cont.¹)

```
571  CCCATCATCTTCGGGATCCTGTTTGCCATCCTCTTGGTGCTGGTCTTTAT  620
     |||||||||||||||||||||||||||||||||||||||||||||||||
642  cccatcatcttcgggatcctgtttgccatcctcttggtgctggtctttat  691

621  CAAAAAGGTGGCCAAGAAGCCAACCAATAAGGCCCCCCAAGCAGG       670
     |||||||||||||||||||||||||||||||||||||||||||||
692  caaaaaggtggccaagaagccaaccaataaggcccccaagcagg        741

671  AACCCCAGGAGATCAATTTTCCCGACGATCTTCCTGGCTCCAACACTGCT  720
     |||||||||||||||||||||||||||||||||||||||||||||||||
742  aaccccaggagatcaatttcccgacgatcttcctggctccaacactgct   791

721  GCTCCAGTGCAGGAGACTTTACATGGATGCCAACCGGTCACCCAGGAGGA  770
     |||||||||||||||||||||||||||||||||||||||||||||||||
792  gctccagtgcaggagactttacatggatgccaaccggtcacccaggagga  841

771  TGGCAAAGAGAGTCGCATCTCAGTGCAGGAGAGACAGTGAGGCTGCACCC  820
     |||||||||||||||||||||||||||||||||||||||||||||||||
842  tggcaaagagagtcgcatctcagtgcaggagagacagtgaggctgcaccc  891
```

Fig. 5 (Cont.²)

```
821 ACCCAGGAGTGTGGCCACGTGGGCAAACAGGCAGTTGGGCCAGAGAGCCTG 870
    ||||||||||||||||||||||||||||||||||||||||||||||||||
892 acccaggagtgtggccacgtgggcaaacaggcagttggccagagagcctg 941

871 GTGCTGCTGCTGTGGCG 890
    ||||||||||| || ||
942 gtgctgctgctgcaggggtg 961
```

Fig. 5 (Cont.³)

```
  1  MVRLPLQCVLWGCLLTAVHPEPPTACREKQYLINSQCCSLCQPGQKLVSD   50
     ||||||||||||||||||||||||||||||||||||||||||||||||||
  1  MVRLPLQCVLWGCLLTAVHPEPPTACREKQYLINSQCCSLCQPGQKLVSD   50

51  CTEFTETECLPCGESEFLDTWNRETHCHQHKYCDPNLGLRVQQKGTSETD  100
     |||||||||||||||||||||||||||||||||||||||||||||||||
 51  CTEFTETECLPCGESEFLDTWNRETHCHQHKYCDPNLGLRVQQKGTSETD  100

101  TICTCEEGWHCTSEACESCVLHRSCSPGFGVKQIATGVSDTIC         143
     |||||||||||||||||||||||||||||||||||         ::
101  TICTCEEGWHCTSEACESCVLHRSCSPGFGVKQIAVRPKTWLC         143
```

Fig. 6

SEQUENCE LISTING

<160> NUMBER OF SEQ ID NOS: 12

<210> SEQ ID NO 1
<211> LENGTH: 526
<212> TYPE: DNA
<213> ORGANISM: Homo sapiens

<400> SEQUENCE: 1

```
atggttcgtc tgcctctgca gtgcgtcctc tggggctgct tgctgaccgc tgtccatcca      60
gaaccaccca ctgcatgcag agaaaaacag tacctaataa acagtcagtg ctgttctttg     120
tgccagccag gacagaaact ggtgagtgac tgcacagagt tcactgaaac ggaatgcctt     180
ccttgcggtg aaagcgaatt cctagacacc tggaacagag agacacactg ccaccagcac     240
aaatactgcg accccaacct agggcttcgg gtccagcaga agggcacctc agaaacagac     300
accatctgca cctgtgaaga aggctggcac tgtacgagtg aggcctgtga gagctgtgtc     360
ctgcaccgct catgctcgcc cggctttggg gtcaagcaga ttgctgtgag accaaagacc     420
tggttgtgca acaggcaggc acaaacaaga ctgatgttgt ctgtggtccc caggatcggc     480
tgagagccct ggtggtgatc cccatcatct tcgggatcct gtttgc                    526
```

<210> SEQ ID NO 2
<211> LENGTH: 1126
<212> TYPE: DNA
<213> ORGANISM: Homo sapiens
<220> FEATURE:
<221> NAME/KEY: misc_feature
<222> LOCATION: (3)..(3)
<223> OTHER INFORMATION:
<221> NAME/KEY: misc_feature
<222> LOCATION: (3)..(3)
<223> OTHER INFORMATION: n = any nuceic acid
<221> NAME/KEY: misc_feature
<222> LOCATION: (1109)..(1109)
<223> OTHER INFORMATION: n = any nucleic acid
<221> NAME/KEY: misc_feature
<222> LOCATION: (1107)..(1107)
<223> OTHER INFORMATION: n = any nucleic acid
<221> NAME/KEY: misc_feature
<222> LOCATION: (1105)..(1105)
<223> OTHER INFORMATION:
<221> NAME/KEY: misc_feature
<222> LOCATION: (1105)..(1105)
<223> OTHER INFORMATION: n = any nucleic acid
<221> NAME/KEY: misc_feature
<222> LOCATION: (1098)..(1098)
<223> OTHER INFORMATION: n = nay nucleic acid

<400> SEQUENCE: 2

```
gtnacatcct tcaaatcgga tctggaagtt ctgttccagg ggccctggg atccccagga       60 attcccggga tggttcgtct gcctctgcag tgcgtcctct ggggctgctt gctgaccgct     120
gtccatccag aaccacccac tgcatgcaga gaaaaacagt acctaataaa cagtcagtgc     180
tgttctttgt gccagccagg acagaaactg gtgagtgact gcacagagtt cactgaaacg     240
```

```
gaatgccttc cttgcggtga aagcgaattc ctagacacct ggaacagaga gacacactgc    300
caccagcaca aatactgcga ccccaaccta gggcttcggg tccagcagaa gggcacctca    360
gaaacagaca ccatctgcac ctgtgaagaa ggctggcact gtacgagtga ggcctgtgag    420
agctgtgtcc tgcaccgctc atgctcgccc ggctttgggg tcaagcagat tgcttgtgag    480
accaaagacc tggttgtgca acaggcaggc acaaacaaga ctgatgttgt ctgtggtccc    540
caagatcggc tgagagccct ggtggtgatc cccatcatct tcgggatcct gtttgccatc    600
ctcttggtgc tggtctttat caaaaaggtg gccaagaagc caaccaataa ggccccccac    660
cccaagcagg aacccagga gatcaatttt cccgacgatc ttcctggctc caacactgct    720
gctccagtgc aggagacttt acatggatgc caaccggtca cccaggagga tggcaaagag    780
agtcgcatct cagtgcagga gagacagtga ggctgcaccc acccaggagt gtggccacgt    840
gggcaaacag gcagttggcc agagagcctg gtgctgctgc tgctgtggcg tgagggtgag    900
gggctggcac tgactgggca tagctccccg cttctgcctg caccctgca gtttgagaca     960 ggagacctgg cactggatgc agaaacagtt caccttgaag aacctctcac ttcaccctgg    1020
agcccatcca gtctcccaac ttgtattaaa gacagaggca gaagctcgag cggccgcatc    1080
gtgactgact gacgatcngc ctcgngngnt tcggtatgac ggtaaa                   1126
```

<210> SEQ ID NO 3
<211> LENGTH: 934
<212> TYPE: DNA
<213> ORGANISM: Murinae gen. sp.
<220> FEATURE:
<221> NAME/KEY: misc_feature
<222> LOCATION: (5)..(5)
<223> OTHER INFORMATION: n = any nucleic acid
<221> NAME/KEY: misc_feature
<222> LOCATION: (796)..(796)
<223> OTHER INFORMATION: n = any nucleic acid
<221> NAME/KEY: misc_feature
<222> LOCATION: (829)..(829)
<223> OTHER INFORMATION: n = any nucleic acid
<221> NAME/KEY: misc_feature
<222> LOCATION: (863)..(863)
<223> OTHER INFORMATION: n = any nucleic acid
<221> NAME/KEY: misc_feature
<222> LOCATION: (881)..(881)
<223> OTHER INFORMATION: n = any nucleic acid
<221> NAME/KEY: misc_feature
<222> LOCATION: (883)..(883)
<223> OTHER INFORMATION: n = any nucleic acid
<221> NAME/KEY: misc_feature
<222> LOCATION: (884)..(884)
<223> OTHER INFORMATION: n = any nucleic acid
<221> NAME/KEY: misc_feature
<222> LOCATION: (891)..(891)
<223> OTHER INFORMATION: n = any nucleic acid
<221> NAME/KEY: misc_feature
<222> LOCATION: (894)..(894)
<223> OTHER INFORMATION: n = any nucleic acid
<221> NAME/KEY: misc_feature
<222> LOCATION: (903)..(903)
<223> OTHER INFORMATION: n = any nucleic acid
<221> NAME/KEY: misc_feature
<222> LOCATION: (921)..(921)
<223> OTHER INFORMATION: n = any nucleic acid
<221> NAME/KEY: misc_feature
<222> LOCATION: (927)..(927)
<223> OTHER INFORMATION: n = any nucleic acid
<221> NAME/KEY: misc_feature
<222> LOCATION: (932)..(932)
<223> OTHER INFORMATION: n = any nucleic acid

<400> SEQUENCE: 3

```
ccttnagggc gcggatccca ggaattcccg ggatggtgtc tttgcctcgg ctgtgcgcgc     60
```

-continued

```
tatgggctg cttgttgaca gcggtccatc tagggcagtg tgttacgtgc agtgacaaac      120
agtacctcca cgatggccag tgctgtgatt tgtgccagcc aggaagccga ctgacaagcc      180
actgcacagc tcttgagaag acccaatgcc acccatgtga ctcaggcgaa ttctcagccc      240
agtggaacag ggagattcgc tgtcaccagc acagacactg tgaacccaat caagggcttc      300
gggttaagaa ggagggcacc gcagaatcag acactgtctg tacctgtaag gaaggacaac      360
actgcaccag caaggattgc gaggcatgtg ctcagcacac gccctgtatc cctggctttg      420
gagttatgga gatggctgtg aggataagaa cttggaggtc ctacagaaag gaacgagtca      480
gactaatgtc atctgtggtt taaagtcccg gatgcgagcc ctgctggtca ttcctgtcgt      540
gatgggcatc ctcatcaccg ttttcggggt gtttctctat atcaaaaagg tggtcaagaa      600
accaaaggat ctcgaggcat gcggtaccaa gcttgtcgag aagtactaga ggatcattaa      660
tcagccatac cacatttgta gaagttttac ttgctttaaa aaaacctccc cacacctccc      720
ccctgaacct gaaacataaa aattgaatgc aattggtggt tggttaactt tggtttaatt      780
ggcagcctta ttaatnggtt tacaaaatta agccaataa gccttcccna aattttcaca       840
aaataaaagc catttttttt ccnactggga tttctaaatt ngnngggttt nggnccaaaa      900
ctnccatcaa aggggatctt natcaanggt cngg                                   934
```

<210> SEQ ID NO 4
<211> LENGTH: 776
<212> TYPE: DNA
<213> ORGANISM: Murinae gen. sp.

<400> SEQUENCE: 4

```
atggtgtctt tgcctcggct gtgcgcgcta tggggctgct tgttgacagc ggtccatcta       60
gggcagtgtg ttacgtgcag tgacaaacag tacctccacg atggccagtg ctgtgatttg      120
tgccagccag gaagccgact gacaagccac tgcacagctc ttgagaagac ccaatgccac      180
ccatgtgact caggcgaatt ctcagcccag tggaacaggg agattcgctg tcaccagcac      240
agacactgtg aacccaatca gggcttcggg ttaagaagg agggcaccgc agaatcagac      300
actgtctgta cctgtaagga aggacaacac tgcaccagca aggattgcga ggcatgtgct      360
cagcacacgc cctgtatccc tggctttgga gttatggaga tggccactga gaccactgat      420
accgtctgtc atccctgccc agtcggcttc ttctccaatc agtcatcact tttcgaaaag      480
tgttatccct ggacaaggtt taaagtcccg gatgcgagcc ctgctggtca ttcctgtcgt      540
gatgggcatc ctcatcacca ttttcggggt gtttctctat atcaaaaagg tggtcaagaa      600
accaaaggat aatgagatgt taccccctgc ggctcgacgg caagatcccc aggagatgga      660
agattatccc ggtcataaca ccgctgctcc agtgcaggag acactgcacg ggtgtcagcc      720
tgtcacacag gaggatggta aagagagtcg catctcagtg caggagcggc aggtga          776
```

<210> SEQ ID NO 5
<211> LENGTH: 788
<212> TYPE: DNA
<213> ORGANISM: Murinae gen. sp.

<400> SEQUENCE: 5

```
atggtgtctt tgcctcggct gtgcgcgcta tggggctgct tgttgacagc ggtccatcta       60
gggcagtgtg ttacgtgcag tgacaaacag tacctccacg atggccagtg ctgtgatttg      120
tgccagccag gaagccgact gacaagccac tgcacagctc ttgagaagac ccaatgccac      180
```

| | |
|---|---:|
| ccatgtgact caggcgaatt ctcagcccag tggaacaggg agattcgctg tcaccagcac | 240 |
| agacactgtg aacccaatca agggcttcgg gttaagaagg gggcaccgc agaatcagac | 300 |
| actgtctgta cctgtaagga aggacaacac tgcaccagca aggattgcga ggcatgtgct | 360 |
| cagcacacgc cctgtatccc tggctttgga gttatggaga tggccactga gaccactgat | 420 |
| accgtctgtc atccctgccc agtcggcttc ttctccaatc agtcatcact tttcgaaaag | 480 |
| tgttatccct ggacaaggtt taaagtcccg gatgcgagcc ctgctggtca ttcctgtcgt | 540 |
| gatgggcatc ctcatcaccg ttttcggggt gtttccctat atcagtgagt gctcaggaga | 600 |
| ggaaagggag ggagggttca gccctgtcga accagcctcc tgactcaccc tcgcaatgtc | 660 |
| ccacacccct tcttcttctc actagaaaag gtggtcaaga aaccaaagga taatgagatc | 720 |
| ttaccccctg cgactcgacg gcaagatccc caggagatgg aagattatcc cggtcataac | 780 |
| accgctgc | 788 |

<210> SEQ ID NO 6
<211> LENGTH: 809
<212> TYPE: DNA
<213> ORGANISM: Murinae gen. sp.

<400> SEQUENCE: 6

| | |
|---|---:|
| atggtgtctt tgcctcggct gtgcgcgcta tggggctgct tgttgacagc ggtccatcta | 60 |
| gggcagtgtg ttacgtgcag tgacaaacag tacctccacg atggccagtg ctgtgatttg | 120 |
| tgccagccag gaagccgact gacaagccac tgcacagctc ttgagaagac ccaatgccac | 180 |
| ccatgtgact caggcgaatt ctcagcccag tggaacaggg agattcgctg tcaccagcac | 240 |
| agacactgtg aacccagtgc gtggggctgc ctgggaaggg atcaagggct tcgggttaag | 300 |
| aaggagggca ccgcagaatc agacactgtc tgtacctgta aggaaggaca acactgcacc | 360 |
| agcaaggatt gcgaggcatg tgctcagcac acgccctgta tccctggctt tggagttatg | 420 |
| gagatggcca ctgagaccac tgataccgtc tgtcatccct gcccagtcgg cttcttctcc | 480 |
| aatcagtcat cacttttcga aaagtgttat ccctggacaa ggtttaaagt cccggatgcg | 540 |
| agccctgctg gtcattcctg tcgtgatggg catcctcatc accattttcg gggtgtttct | 600 |
| ctatatcaaa aagtggtca agaaaccaaa ggataatgag atgttacccc ctgcggctcg | 660 |
| acggcaagat ccccaggaga tggaagatta tcccggtcat aacaccgctg ctccagtgca | 720 |
| ggagacactg cacgggtgtc agcctgtcac acaggaggat ggtaaagaga gtcgcatctc | 780 |
| agtgcaggag cggcaggtga cagacagca | 809 |

<210> SEQ ID NO 7
<211> LENGTH: 160
<212> TYPE: PRT
<213> ORGANISM: Homo sapiens

<400> SEQUENCE: 7

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His

```
                  65                  70                  75                  80
Lys Tyr Cys Asp Pro Asn Leu Gly Leu Arg Val Gln Gln Lys Gly Thr
                            85                  90                  95

Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
            115                 120                 125

Phe Gly Val Lys Gln Ile Ala Val Arg Pro Lys Thr Trp Leu Cys Asn
        130                 135                 140

Arg Gln Ala Gln Thr Arg Leu Met Leu Ser Val Val Pro Arg Ile Gly
145                 150                 155                 160

<210> SEQ ID NO 8
<211> LENGTH: 246
<212> TYPE: PRT
<213> ORGANISM: Homo sapiens

<400> SEQUENCE: 8

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
            115                 120                 125

Phe Gly Val Lys Gln Ile Ala Cys Glu Thr Lys Asp Leu Val Val Gln
        130                 135                 140

Gln Ala Gly Thr Asn Lys Thr Asp Val Val Cys Gly Pro Gln Asp Arg
145                 150                 155                 160

Leu Arg Ala Leu Val Val Ile Pro Ile Ile Phe Gly Ile Leu Phe Ala
                165                 170                 175

Ile Leu Leu Val Leu Val Phe Ile Lys Lys Val Ala Lys Lys Pro Thr
            180                 185                 190

Asn Lys Ala Pro His Pro Lys Gln Glu Pro Gln Glu Ile Asn Phe Pro
        195                 200                 205

Asp Asp Leu Pro Gly Ser Asn Thr Ala Ala Pro Val Gln Glu Thr Leu
    210                 215                 220

His Gly Cys Gln Pro Val Thr Gln Glu Asp Gly Lys Glu Ser Arg Ile
225                 230                 235                 240

Ser Val Gln Glu Arg Gln
                245

<210> SEQ ID NO 9
<211> LENGTH: 156
<212> TYPE: PRT
<213> ORGANISM: Murinae gen. sp.
```

```
<400> SEQUENCE: 9

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Val Arg Ile Arg Thr Trp Arg Ser Tyr
    130                 135                 140

Arg Lys Glu Arg Val Arg Leu Met Ser Ser Val Val
145                 150                 155

<210> SEQ ID NO 10
<211> LENGTH: 203
<212> TYPE: PRT
<213> ORGANISM: Murinae gen. sp.

<400> SEQUENCE: 10

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Arg Phe Lys Val Pro Asp Ala Ser Pro Ala Gly
                165                 170                 175

His Ser Cys Arg Asp Gly His Pro His His Phe Arg Gly Val Ser
            180                 185                 190

Leu Tyr Gln Lys Gly Gly Gln Glu Thr Lys Gly
    195                 200
```

```
<210> SEQ ID NO 11
<211> LENGTH: 195
<212> TYPE: PRT
<213> ORGANISM: Murinae gen. sp.

<400> SEQUENCE: 11
```

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
            35                  40                  45

Ser His Cys Thr Ala Leu Glu Lys Thr Gln Cys His Pro Cys Asp Ser
        50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Arg Phe Lys Val Pro Asp Ala Ser Pro Ala Gly
                165                 170                 175

His Ser Cys Arg Asp Gly His Pro His His Arg Phe Arg Gly Val Ser
            180                 185                 190

Leu Tyr Gln
        195

```
<210> SEQ ID NO 12
<211> LENGTH: 211
<212> TYPE: PRT
<213> ORGANISM: Murinae gen. sp.

<400> SEQUENCE: 12
```

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
            35                  40                  45

Ser His Cys Thr Ala Leu Glu Lys Thr Gln Cys His Pro Cys Asp Ser
        50                  55                  60

Gly Glu Phe Ser Ala Gln Trp Asn Arg Glu Ile Arg Cys His Gln His
65                  70                  75                  80

Arg His Cys Glu Pro Ser Ala Trp Gly Cys Leu Gly Arg Asp Gln Gly
                85                  90                  95

Leu Arg Val Lys Lys Glu Gly Thr Ala Glu Ser Asp Thr Val Cys Thr
            100                 105                 110

Cys Lys Glu Gly Gln His Cys Thr Ser Lys Asp Cys Glu Ala Cys Ala
        115                 120                 125

-continued

```
Gln His Thr Pro Cys Ile Pro Gly Phe Gly Val Met Glu Met Ala Thr
    130                 135                 140

Glu Thr Thr Asp Thr Val Cys His Pro Cys Pro Val Gly Phe Phe Ser
145             150                 155                     160

Asn Gln Ser Ser Leu Phe Glu Lys Cys Tyr Pro Trp Thr Arg Phe Lys
            165                 170                 175

Val Pro Asp Ala Ser Pro Ala Gly His Ser Cys Arg Asp Gly His Pro
            180             185                 190

His His His Phe Arg Gly Val Ser Leu Tyr Gln Lys Gly Gly Gln Glu
        195             200                 205

Thr Lys Gly
    210
```

SPLICE VARIANTS OF CD40-RECEPTOR

This application is the national phase under 35 U.S.C. § 371 of PCT International Application No. PCT/IL00/00427 which has an International filinq date of Jul. 19, 2000, which designated the United States of America and was published in English.

FIELD OF THE INVENTION

The present invention concerns novel nucleic acid sequences, vectors and host cells containing them, amino acid sequences encoded by said sequences, and antibodies reactive with said amino acid sequences, as well as pharmaceutical compositions comprising any of the above. The present invention further concerns methods for detecting nucleic acid and amino acid sequences in a sample.

BACKGROUND OF THE INVENTION

CD40 is a cell surface receptor, which belongs to the TNF-R family, and which was first identified and functionally characterized on B lymphocytes. However, in recent years it has become clear that CD40 is more widely expressed, including expression on monocytes, dendritic cells, endothelial cells and epithelial cells. Therefore it is now thought that CD40 plays a more general role in immune regulation.

The CD40 protein is a 45–50 kDa glycoprotein of 277 AA, the 193 AA extracellular domain is composed of four imperfect repeats of about 40 residues, anchored by a superimposable pattern of six cysteines. This organization is found in the other members of the TNF-R family.

CD40 is expressed by multiple cell types. In the hematopoietic system, it is expressed on CD45 hematopoietic progenitors, B cell progenitors, mature B lymphocytes, plasma cells, monocytes, dendritic cells, cosinophils, basophils and on some T lymphocytes. CD40 is also expressed on non-hematopoietic cells such as endothelial cells, fibroblasts and epithelial cells.

Expression cloning using a CD40-Fc fusion protein allowed the isolation of a CD40-ligand (CD40-L) from activated T cells. The human CD40-L is a polypeptide of 261 AA including a 215 AA extracellular domain with five cysteines. CD40-L is a member of the Tumor Necrosis Factor family.

CD40-R bound to its ligand activates protein-tyrosine kinases, including Lyn and Syk and induces the tyrosine phosphorylation of multiple substrates including phosphatidylinositol 3-kinase and phospholipase Cγ2.

CD40 also interacts with TRAF3 protein (TNF-R Associated Factor-3), also identified under the name CRAF1, CD40 bp, LAP1 and CAP1 (18-21). TRAF3 is a 62 kD intracellular protein which is expressed in almost all cell types. The protein contains several functional domains which might be involved in signal transduction.

In addition, CD40 has been demonstrated to associate with TRAF2, a molecule which also associates with TNF-R2. The induction of NF-$_\kappa$B activation via CD40 cross-linking (and also via TNF-R2) could be attributed to TRAF2 signaling.

CD40 ligation activates resting B cells as shown by increase in size and expression of new surface molecules involved in homotypic and heterotypic aggregation (CD23, VLA-4), as well as T cell costimulation (CD80/CD86).

Furthermore, CD40-activated B cells secrete a panel of cytokines which may act as autocrine and paracrine growth and differentiation factors.

CD40 is further known to be expressed on professional antigen presenting cells such as monocytes and dendritic cells, and its ligation to the above cells results in secretion of multiple proteins including cytokines such as IL1, IL5, IL8 IL10, IL12, $TNF_\alpha$, $MiPl_\alpha$, as well as enzymes such as matrix metalloproteinase (MMP).

The importance of this receptor-ligand pair for the cellular immune response, has been demonstrated by the diminished immunity against several pathogens in CD40 and CD40-L knockout mice. In keeping with this, CD40 ligation turns on monocyte tumoricidal activity as well as NO synthesis.

Administration of antibodies to CD40-L has been shown to prevent the establishment of autoimmune symptoms in various murine models including: (1) collagen type II-induced arthritis: a model for human rheumatoid arthritis; (2) lupus nephritis in lupus prone mice that represent models for the systemic lupus erythematosus; (3) protcolipoprotein induced experimental encephalomyelitis: a model of human multiple sclerosis.

Administration of anti-CD40-L antibodies further has been demonstrated to prevent the development of graft versus host disease (GVHD) that occurs as a major complication of allogeneic bone marrow transplantation (van Kooten, C. and Banchereau, J., *Frontiers in Bioscience*, d1-11 Jan. 1, (1997)).

GLOSSARY

In the following description and claims use will be made, at times, with a variety of terms, and the meaning of such terms as they should be construed in accordance with the invention is as follows:

"CD40R Variants nucleic acid sequences"—the sequence shown in any one of SEQ ID NO: 1 to SEQ ID NO: 6 sequences having at least 90% identity (see below) to said sequences and fragments (see below) of the above sequences of least 20 b.p. long. These sequences are sequences coding for a novel naturally occurring, alternative splice variants of the native and known CD40R, depicted in the Swiss Prot as CD40_HUMAN under Accession Number P25942 which is the sequence coding for the human 45–50 kDa glycoprotein of 277 amino acid. It should be emphasized that the novel variants of the present invention are naturally occurring sequences resulting from alternative splicing of the CD40R gene and not merely truncated, mutated or fragmented form of the gene.

The description of the CD40R variants and their difference from the original sequence is summarized in Table 1 as follows:

TABLE 1

| SEQ ID NO: | New variant internal name | Length (amino acids) | Description of the variation (comparing to the original sequences |
|---|---|---|---|
| 1 | | 160 | Has the extracellular domain of the native CD40 gene from signal peptide up to the position of the amino acid before the transmembrane region. |
| 2 | | 246 | Has the extracellular domain of the native CD40 gene from signal peptide up to the position of the amino acid before the transmembrane region. |

TABLE 1-continued

| SEQ ID NO: | New variant internal name | Length (amino acids) | Description of the variation (comparing to the original sequences |
|---|---|---|---|
| 3 | Mcd40-pFB1-1-5 | 156 | Contains 135 N-terminal amino acids, including entire TNFR-Cys repeats 1 and 2, and part of the TNFR-Cys repeat 3. Alternative 21 amino acids at the C terminus. Missing the TNFR-Cys repeat #4, part of the TNFR-Cys repeat #3, the TM domain and the cytoplasmic domain |
| 4 | MCD40Alt8 | 203 | Contains 165 N-terminal amino acids, including entire TNFR-Cys repeats 1, 2, 3 and part of the TNFR-Cys repeat 4. Alternative 38 amino acids at the C terminus. Missing part of TNFR-Cys repeat #4, the TM domain and the cytoplasmic domain. |
| 5 | MCD40Alt19 | 195 | Contains 165 N-terminal amino acids, including entire TNFR-Cys repeats 1, 2, 3 and part of the TNFR-Cys repeat 4. Alternative 30 amino acids at the C terminus. Missing part of TNFR-Cys repeat #4, the TM domain and the cytoplasmic domain. |
| 6 | MCD40Alt6Corecte | 211 | Contains 165 N-terminal amino acids, including entire TNFR-Cys repeats 1, 2, 3 and part of the TNFR-Cys repeat 4. Insertion of 9 amino acids at the position #86 of the wild type protein (instead of the original Asn). Alternative 30 amino acids at the C terminus. Missing part of TNFR-Cys repeat #4, the TM domain and the cytoplasmic domain. |

SEQ ID NOS. 1 and 2 are from human source origin.
SEQ ID NOS: 4–6 are for mouse ortholog sequence.

"CD40R Variants products"—also referred at times as the "CD40R variants proteins" or "CD40R variants polypeptides"—is an amino acid sequence encoded by the CD40R variants nucleic acid sequences which is a naturally occurring mRNA sequence obtained as a result of alternative splicing. The amino acid sequences may be a peptide, a protein, as well as peptides or proteins having chemically modified amino acids (see below) such as a glycopeptide or glycoprotein. The CD40R variants products are shown in any one of SEQ ID NO: 7 to SEQ ID NO: 12. The term also includes homologs (see below) of said sequences in which one or more amino acids has been added, deleted, substituted (see below) or chemically modified (see below) as well as fragments (see below) of this sequence having at least 10 amino acids. As indicated above, this sequence refers to the extracellular domain of the CD40R.

"Fragments of CD40 variants nucleic acid sequences"—a partial sequence of any one of SEQ ID NO: 1 to SEQ ID NO: 6 which includes the regions which contains the variation in nucleotides between the variant and the original sequences. These regions (in the amino acid level) are as depicted in the above Table 1.

"Fragments of CD40R variant product"—amino acid sequences coded by the above nucleic acid fragment, containing regions by which the variant differs from the original sequence as indicated in Table 1.

"Nucleic acid sequence" . a sequence composed of DNA nucleotides, RNA nucleotides or a combination of both types and may includes natural nucleotides, chemically modified nucleotides and synthetic nucleotides.

"Amino acid sequence" . a sequence composed of any one of the 20 naturally appearing amino acids, amino acids which have been chemically modified (see below), or composed of synthetic amino acids.

"Homologues of variants/products"—amino acid sequences of variants in which one or more amino acids has been added, deleted or replaced. The altered amino acid shall be in regions where the variant differs from the original sequence, for example, according to the explanation in Table 1.

"Conservative substitution"—refers to the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class 1 (Cys); Class II (Ser, Thr, Pro, Ala, Gly); Class III (Asn, Asp, Gln, Glu); Class IV (His, Arg, Lys); Class V (ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class III residue such as Asp, Asn, Glu, or Gln.

"Chemically modified"—when referring to the product of the invention, means a product (protein) where at least one of its amino acid resides is modified either by natural processes, such as processing or other post-translational modifications, or by chemical modification techniques which are well known in the art Among the numerous known modifications typical, but not exclusive examples include:
  acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

"Biologically active"—refers to the variant product having some sort of biological activity, for example, capability of binding to the CD40 ligand (CD40-L) or to other agonists of the original CD40R as known.

"Immunologically active" defines the capability of a natural, recombinant or synthetic varient product, or any fragment thereof, to induce a specific immune response in appropriate animals or cells and to bind with specific antibodies. Thus, for example, an immunologically active fragment of variant product denotes a fragment which retains some or all of the immunological properties of the variant product, e.g can bind specific anti-variant product antibodies or which can elicit an immune response which will generate such antibodies or cause proliferation of specific immune cells which produce variant.

"Optimal alignment"—is defined as an alignment giving the highest percent identity score. Such alignment can be performed using a variety of commercially available sequence analysis programs, such as the local alignment program LALIGN using a ktup of 1, default parameters and the default PAM. A preferred alignment is the one performed using the CLUSTAL-W program from MacVector™, operated with an open gap penalty of 10.0, an extended gap penalty of 0.1, and a BLOSUM similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence). In case of alignments of known gene sequences with that of the new variant, the optimal alignment invariably included aligning the identical parts of both sequences together, then keeping apart and unaligned the sections of the sequences that differ one from the other.

"Having at least 90% identity"—with respect to two amino acid or nucleic acid sequence sequences, refers to the percentage of residues that are identical in the two sequences when the sequences are optimally aligned. Thus, 90% amino acid sequence identity means that 90% of the amino acids in two or more optimally aligned polypeptide sequences are identical.

"Isolated nucleic acid molecule having an variant nucleic acid sequence"—is a nucleic acid molecule that includes the CD40R variant nucleic acid coding sequence. Said isolated nucleic acid molecule may include the CD40R variant nucleic acid sequence as an independent insert; may include the CD40R variant nucleic acid sequence fused to an additional coding sequences, encoding together a fusion protein in which the variant coding sequence is the dominant coding sequence (for example, the additional coding sequence may code for a signal peptide); the CD40R variant nucleic acid sequence may be in combination with non-coding sequences, e.g., introns or control elements, such as promoter and terminator elements or 5' and/or 3' untranslated regions, effective for expression of the coding sequence in a suitable host; or may be a vector in which the CD40R variant protein coding sequence is a heterologous.

"Expression vector"—refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

"Antibody"—refers to IgG, IgM, IgD, IgA, and IgG antibody. The definition includes polygonal antibodies or monoclonal antibodies. This term refers to whole antibodies or fragments of the antibodies comprising the antigen-binding domain of the anti-variant product antibodies, e.g. antibodies without the Fc portion, single chain antibodies, fragments consisting of essentially only the variable, antigen-binding domain of the antibody, etc.

"Treating a disease"—refers to administering a therapeutic substance effective to ameliorate symptoms associated with a disease, to lessen the severity or cure the disease, or to prevent the disease from occurring.

"Detection"—refers to a method of detection of a disease, disorder, pathological or normal condition. This term may refer to detection of a predisposition to a disease as well as for establishing the prognosis of the patient by determining the severity of the disease.

"Probe"—the CD40R variant nucleic acid sequence, or a sequence complementary therewith, when used to detect presence of other similar sequences in a sample or of sequences having some homology with this sequence. The detection is carried out by identification of hybridization complexes between the probe and the assayed sequence. The probe may be attached to a solid support or to a detectable label.

"Original CD40R"—the amino acid or nucleic acid sequence from which the CD40R variants of the invention have been varied as a result of alternative slicing. The original nucleic sequence is the sequence of the human CD40 receptor depicted as CD40_HUMAN Swiss Prot under Accession Number P25942 and the original amino acid sequence is the sequence encoded by it.

SUMMARY OF THE INVENTION

The present invention is based on the finding of six novel, naturally occurring splice variants of the CD40 receptor (CD40R), which are naturally occurring sequences obtained by alternative splicing of the known CD40R gene depicted as CD40_HUMAN Swiss Prot under Accession Number P25942. The novel splice variants of the invention are not merely truncated forms, or fragments of the known gene, but rather novel sequences which naturally occur within the body of individuals. These novel variants in fact contain only the extracellular domains of the original CD40R.

The term "alternative splicing" in the context of the present invention and claims refers to: exon exclusion, and deletion of terminal sequences in the variants as compared to the original sequence.

The novel CD40R variants of the invention retains the ligand-binding (extracellular) domain of the original CD40R, and thus are capable of binding to its ligands (for example the CD40-L) and decreasing in the individual the amounts of such free ligands available for binding to the original CD40R Thus the CD40R variants of the invention may act as a "scavengers" of the CD40 ligand, since they can bind those ligands without causing signal transduction due to said binding, and thus effectively lowers the amount of said ligands. Since the variants are secreted they can exert their scavenging effect even in body fluids.

The novel CD40R variants may also serve for detection purposes, i.e. their presence or level may be indicative of a disease, disorder, pathological or normal condition involving CD40 receptor such as inflammatory diseases, autoimmune diseases involving the immune system, pathological conditions, or alternatively the ratio between the variants' level and the level of the original CD40R peptide from which they have been varied, or the ratio of any variants with respect to each other may be indicative to such a disease, disorder, pathological or normal condition.

For example, for detectional purposes, it is possible to establish differential expression of the CD40R variants in various tissues as compared to the original CD40R. The variants (either each separately or both) may be expressed mainly in one tissue, while the original CD40R sequence from which they have been varied, may be expressed mainly in another tissue. Understanding of the distribution of the variants as compared to the original sequence or as compared to one another in various tissues may be helpful in basic research, for understanding the physiological function of the gene as well as may help in targeting pharmaceuticals or developing pharmaceuticals.

The detection may by determination of the presence or the level of expression of the CD40R variants within a specific cell population, comparing said presence or level between various cell types in a tissue, between different tissues and between individuals.

Thus the present invention provides by its first aspect, a novel isolated nucleic acid molecule comprising or consisting of the sequence of any one of SEQ ID NO: 1 to SEQ ID NO: 6, fragments of said coding sequence having at least 20 nucleic acids or a molecule comprising a sequence having at least 90%, identity to SEQ ID NO: 1 to SEQ ID NO: 6.

The present invention further provides a protein or polypeptide comprising or consisting of an amino acid sequence encoded by any of the above nucleic acid sequences, termed herein "CD40R variant product", for example, an amino acid sequence having the sequence as depicted in any one of SEQ ID NO:7 to SEQ ID NO:12, fragments of the above amino acid sequence having a length of at least 10 amino acids coded by the above fragments of the nucleic acid, as well as homologues of the above a=ino acid sequences in which one or more of the amino acid residues has been substituted (by conservative or non-conservative substitution) added, deleted, or chemically modified.

The present invention further provides nucleic acid molecule comprising or consisting of a sequence which encodes the above amino acid sequences, (including the fragments and homologues of the amino acid sequences). Due to the degenerative nature of the genetic code, a plurality of alternative nucleic acid sequences, beyond the one depicted by any one of SEQ ID NO: 1 to SEQ ID NO:6, can code for the amino acid sequence of the invention. Those alternative nucleic acid sequence which code for the same amino acid sequences depicted any one of the sequences SEQ ID NO:7 to SEQ ID NO: 12 are also an aspect of the of the present invention.

The present invention further provides expression vectors and cloning vectors comprising any of the above nucleic acid sequences, as well as host cells transfected by said vectors.

The present invention still further provides pharmaceutical compositions comprising, as an active ingredient, said nucleic acid molecules, said expression vectors, or said protein or polypeptide.

These pharmaceutical compositions are suitable for the treatment of diseases and pathological conditions, which can be ameliorated or cured by decreasing the levels of any one of the ligands of the original CD40R. By the term "ligand" it is meant not only the CD40-L itself, but any other compounds such as TRAF3 TRAF2 which are known to interact with the CD40 receptor. Examples of such diseases are: autoimmune diseases such as arthritis, rheumatoid arthritis, lupus, (SLE), and multiple sclerosis. The compositions may also be used to prevent development of graph versus host disease (GVHD) encountered after bone-marrow tansplantations.

The CD40R product may also be used for screening or constructing pharmaceuticals with improved specificity. Targeting pharmaceuticals to specific tissues (which express one variant), or targeting them against one condition (in which a particular variant is expressed) may be aided by the variants of the invention which enable screening or constructing pharmaceuticals with improved tissue, or condition specificity.

By a second aspect, the present invention provides a nucleic acid molecule comprising or consisting of a non-coding sequence which is complementary to that of any one of SEQ ID NO:1 to SEQ ID NO:6, or complementary to a sequence having at least 90% identity to said sequences or a fragment of said sequences. The complementary sequence may be a DNA sequence which hybridizes with the sequences of SEQ of ID NO: 1 to SEQ ID NO:6 or hybridizes to a portion of those sequences having a length sufficient to inhibit the transcription of the complementary sequences. The complementary sequence may be a DNA sequence which can be transcribed into an mRNA being an antisense to the mRNA transcribed from SEQ ID NO:1 to SEQ ID NO:6 or into an mRNA which is an antisense to a fragment of the mRNA transcribed from SEQ ID NO:1 to SEQ ID NO:6 which has a length sufficient to hybridize with the mRNA transcribed from any one of SEQ ID NO:1 to SEQ ID NO:6, so as to inhibit its translation. The complementary sequence may also be the mRNA or the fragment of the mRNA itself.

The nucleic acids of the second aspect of the invention may be used for therapeutic or diagnostic applications for example as probes used for the detection of the CD40R variants of the invention. The presence of the CD40R variants transcripts or the level of the variants transcripts may be indicative of a multitude of diseases, disorders and various pathological as well as normal conditions. In addition, the ratio of the level of the transcripts of the variants of the invention may also be compared to that of the transcripts of the original CD40R sequences from which they have been varied or the ratio of each other, and said ratio may be indicative to a multitude of diseases, disorders and various pathological and normal conditions. Comparison may be aided by the fact that while the known CD40 receptor has both cytoplasmic and extracellular regions the variants of the invention have essentially only extracellular regions and are thus secreted soluble.

The present invention also provides expression vectors comprising any one of the above defined complementary nucleic acid sequences and host cells transfected with said nucleic acid sequences or vectors, being complementary to those specified in the first aspect of the invention.

The invention also provides anti-variant product antibodies, namely antibodies directed against the CD40R variants products which specifically bind to said CD40R variants products. Said antibodies are useful both for diagnostic and therapeutic purposes. For example said antibodies may be as an active ingredient in a pharmaceutical composition as will be explained below.

The present invention also provides pharmaceutical compositions comprising, as an active ingredient, the nucleic acid molecules which comprise or consist of said complementary sequences, or of a vector comprising said complementary sequences. The pharmaceutical composition thus provides pharmaceutical compositions comprising, as an active ingredient, said anti-variant product antibodies.

According to the third aspect of the invention the present invention provides methods for detecting the level of the transcripts (mRNA) of said CD40R variants product in a body fluid sample, or in a specific tissue sample, for example by use of probes comprising or consisting of said coding sequences; as well as methods for detecting levels of expression of said product in tissue, e.g. by the use of antibodies capable of specifically reacting with the CD40 variants products of the invention. Detection of the level of the expression of the CD40 variants of the invention in particular as compared to that of the original sequence from which it was varied or compared to each other may be indicative of a plurality of physiological or pathological conditions.

The method, according to this latter aspect, for detection of a nucleic acid sequence which encodes the CD40R variants products in a biological sample, comprises the steps of:

(a) providing a probe comprising at least one of the nucleic acid sequences defined above;

(b) contacting the biological sample with said probe under conditions allowing hybridization of nucleic acid sequences thereby enabling formation of hybridization complexes;

(c) detecting hybridization complexes, wherein the presence of the complex indicates the presence of nucleic acid sequence encoding the CD40R variants products in the biological sample.

The method as described above is qualitative, i.e. indicates whether the transcripts are present in or absent from the sample. The method can also be quantitative, by determining the level of hybridization complexes and then calibrating said levels to determining levels of transcripts of the desired variants in the sample.

Both qualitative and quantitative determination methods can be used for diagnostic, prognostic and therapy planning purposes.

By a preferred embodiment the probe is part of a nucleic acid chip used for detection purposes, i.e. the probe is a part of an array of probes each present in a known location on a solid support.

The nucleic acid sequences used in the above method may be a DNA sequence an RNA sequence, etc; they may be a coding or a sequence or a sequence complementary thereto (for respective detection of RNA transcripts or coding-DNA sequences). By quantization of the level of hybridization complexes and calibrating the quantified results it is possible also to detect the level of the transcripts in the sample.

Methods for detecting mutations in the region coding for the CD40R variants products are also provided, which may be methods carried-out in a binary fashion, namely merely detecting whether there is any mismatches between the normal variant nucleic acid sequence of the invention and the one present in the sample, or carried-out by specifically detecting the nature and location of the mutation.

The present invention also concerns a method for detecting the CD40R variants products in a biological sample, comprising the steps of:

(a) contacting with said biological sample the antibody of the invention, thereby forming an antibody-antigen complex; and (b) detecting said antibody-antigen complex wherein the presence of said antibody-antigen complex correlates with the presence of the CD40R variants products in said biological sample.

As indicated above, the method can be quantitized to determine the level or the amount of the CD40R variants in the sample, alone or in comparison to the level of the original CD40R amino acid sequence from which it was varied, and qualitative and quantitative results may be used for diagnostic, prognostic and therapy planning purposes.

BRIEF DESCRIPTION OF THE DRAWING

FIG. 1 shows multiple alignment of four amino acid sequences ID NOS: 3–6 of mouse origin (depicted in SEQ ID NO:9 to SEQ ID NO:12 to each other and to the original sequence;

FIG. 4 shows comparison by alignment of the original CD40R nucleic acid sequence as obtained from Swiss Prot Accession No. 25942 and SEQ ID NO:1;

FIG. 5 shows a comparison of the original CD40 nucleic acid sequence and SEQ ID NO:2; and FIG. 6 shows comparison by alignment of the original CD40R amino acid sequence and SEQ ID NO:7.

DETAILED DESCRIPTION OF PREFERRED EMBODIMENTS

EXAMPLE I

CD40R Variants Nucleic Acid Sequence

Figure 2:
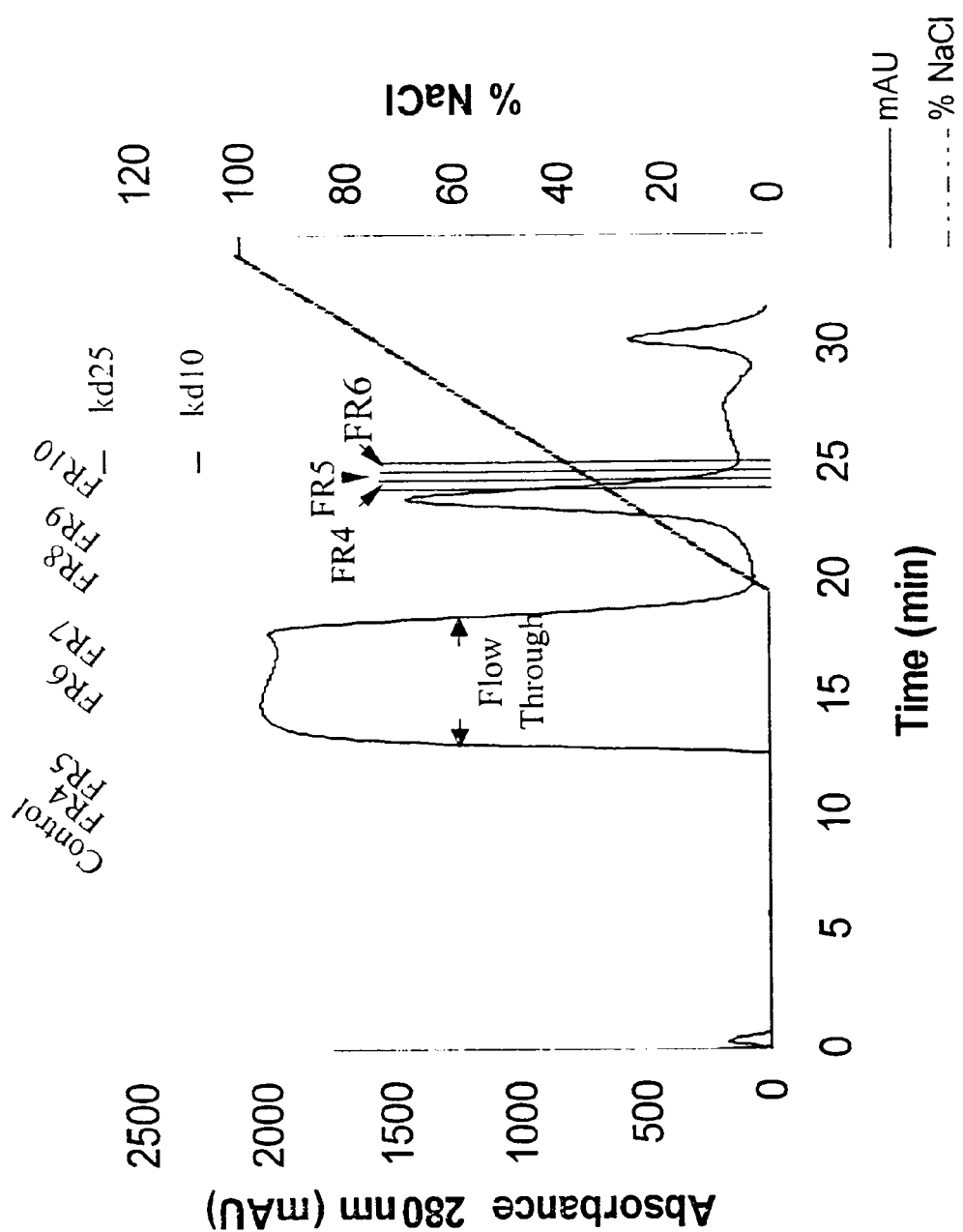
FIG. 2 shows Western blot analysis (top) of St-9 cells infected with CD40 expression vectors and an abnormal spectrum at 280 nm as a function of time.

The nucleic acid sequences of the invention include nucleic acid sequences which encode CD40R variants products and fragments and analogs thereof. The nucleic acid sequences may alternatively be sequences complementary to the above coding sequences, or to regions of said coding sequence. The length of the complementary sequences is sufficient to avoid the expression of the coding sequence. The nucleic acid sequences may be in the form of RNA or in the form of DNA, and include messenger RNA, synthetic RNA and DNA, cDNA and genomic DNA. The DNA may be double-stranded or simple-stranded, and if single-stranded may be the coding strand or the non-coding (antisense, complementary) strand. The nucleic acid sequences may also both include dNTPs, rNTPs as well as non naturally occurring sequences. The sequence may also be a part of a hybrid between an amino acid sequence and a nucleic acid sequence.

In a general embodiment, the nucleic acid sequence has at least 90%, identity with any one of the sequence identified as SEQ ID NO:1 to SEQ ID NO:6.

The nucleic acid sequences may include the coding sequence by itself. By another alternative the coding region may be in combination with additional coding sequences, such as those coding for fusion protein or signal peptides, in combination with non-coding sequences, such as introns and control elements, promoter and terminator elements or 5' and/or 3' untranslated regions, effective for expression of the coding sequence in a suitable host, and/or in a vector or host environment in which the variant nucleic acid sequences is introduced as a heterologous sequence.

The nucleic acid sequences of the present invention may also have the CD40R variants products coding sequences fused in-frame to a marker sequence which allows for purification of the variant product. The marker sequence may be, for example, a hexahistidine tag to provide for purification of the mature polypeptide fused to the marker in the case of a bacterial host, or, the marker sequence may be a hemagglutinin (HA) tag when a mammalian host, e.g. COS-7 cells, is used. The HA tag corresponds to an epitope derived from the influenza hemagglutinin protein (Wilson, I., et al. *Cell* 37:767 (1984)).

Also included in the scope of the invention are fragments as defined above also referred to herein as oligonucleotides, typically having at least 20 bases, preferably 20–30 bases corresponding to a region of the coding-sequence nucleic acid sequence. The fragments may be used as probes, primers, and when complementary also as antisense agents, and the like, according to known methods.

As indicated above, the nucleic acid sequence may be substantially a depicted in SEQ ID NO:1 to SEQ ID NO:6 or fragments thereof or sequences having at least 90% identity to the above sequence as explained above. Alternatively, due to the degenerative nature of the genetic code, the sequence may be a sequence coding for any one of the amino acid sequence of SEQ ID NO:7 or SEQ ID NO:12, or fragments or analogs of said amino acid sequence.

A. Preparation of Nucleic Acid Sequences

The nucleic acid sequences may be obtained by screening cDNA libraries using oligonucleotide probes which can hybridize to or PCR-amplify nucleic acid sequences which encode the CD40R variants products disclosed above. cDNA libraries prepared from a variety of tissues are commercially available and procedures for screening and isolating cDNA clones are well-known to those of skill in the art. Such techniques are described in, for example, Sambrook et al. (1989) Molecular Cloning: A Laboratory Manual (2nd Edition), Cold Spring Harbor Press, Plainview, N.Y. and Ausubel FM et al. (1989) Current Protocols in Molecular Biology, John Wiley & Sons, New York, N.Y.

The nucleic acid sequences may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the RACE method using, for example, the Marathon RACE kit (Clontech, Cat. # K1802-1).

Alternatively, the technique of "restriction-site" PCR (Gobinda et al. *PCR Methods Applic.* 2:318–22, (1993)), which uses universal primers to retrieve flanking sequence adjacent a known locus, may be employed. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia, T. et al., *Nucleic Acids Res.* 16:8186, (1988)). The primers may be designed using OLIGO(R) 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Capture PCR (Lagerstrom, M. et al., *PCR Methods Applic.* 1:111–19, (1991)) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker, J. D., et al., *Nucleic Acids Res.*, 19:3055-60, (1991)). Additionally, one can use PCR, nested primers and PromoterFinder™ libraries to "walk in" genomic DNA (PromoterFinder™; Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes.

A randomly primed library may be particularly useful if an oligo d(T) library does not yield a full-length cDNA. Genomic libraries are useful for extension into the 5' non-translated regulatory region.

The nucleic acid sequences and oligonucleotides of the invention can also be prepared by solid-phase methods, according to known synthetic methods. Typically, fragments of up to about 100 bases are individually synthesized, then joined to form continuous sequences up to several hundred bases.

B. Use of CD40R Variants Nucleic Acid Sequences for the Production of CD40R Variants Products In accordance with the present invention, nucleic acid sequences specified above may be used as recombinant DNA molecules that direct the expression of CD40R variant products.

As will be understood by those of skill in the art, it may be advantageous to produce CD40R variants product-encoding nucleotide sequences possessing codons other than those which appear in SEQ ID NO:1 to SEQ ID NO:6 which are those which naturally occur in the human genome. Codons preferred by a particular prokaryotic or eukaryotic host (Murray, E. et al. *Nuc Acids Res.,* 17:477-508, (1989)) can be selected, for example, to increase the rate of variant product expression or to produce recombinant RNA transcripts having desirable properties, such as a longer half-life, than transcripts produced from naturally occurring sequence.

The nucleic acid sequences of the present invention can be engineered in order to alter a CD40R variants products coding sequences for a variety of reasons, including but not limited to, alterations which modify the cloning, processing and/or expression of the product. For example, alterations may be introduced using techniques which are well known in the art, e.g., site-directed mutagenesis, to insert new restriction sites, to alter glycosylation patterns, to change codon preference, etc.

The present invention also includes recombinant constructs comprising one or more of the sequences as broadly described above. The constructs comprise a vector, such as a plasmid or viral vector, into which nucleic acid sequences of the invention have been inserted, in a forward or reverse orientation. In a preferred aspect of this embodiment, the constructs further comprise regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al., (supra).

The present invention also relates to host cells which are genetically engineered with vectors of the invention, and the production of the product of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the expression of the variant nucleic acid sequence. The culture conditions, such as temperature, pH and the like, are those previously used with the host cell selected for expression, and will be apparent to those skilled in the art.

The nucleic acid sequences of the present invention may be included in any one of a variety of expression vectors for expressing a product. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: LTR or SV40 promoter, the E. coli lac or trp promoter, the phage lambda PL promoter, and other promoters known to control expression of genes in prokaryotic or eukaryotic cells or their viruses. The expression vectors also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vectors containing the appropriate DNA sequence as described above, as well as an appropriate promoter or control sequence, may be employed to transform an appropriate host to permit the host to express the protein. Examples of appropriate expression hosts include: bacterial cells, such as E. coli, Streptomyces, Salmonella typhimurium; fungal cells, such as yeast; insect cells such as Drosophila and Spodoptera Sf9; animal cells such as CHO, COS, HEK 293 or Bowes melanoma; adenoviruses; plant cells, etc. The selection of an appropriate host is deemed to be within the scope of those skilled in the art from the teachings herein. The invention is not limited by the host cells employed.

In bacterial systems, a number of expression vectors may be selected depending upon the use intended for the CD40R variant product. For example, when large quantities of CD40R variant product are needed for the induction of antibodies, vectors which direct high level expression of fusion proteins that are readily purified may be desirable. Such vectors include, but are not limited to, multifunctional E. coli cloning and expression vectors such as Bluescript(R) (Stratagene), in which the CD40R variants polypeptides coding sequence may be ligated into the vector in-frame with sequences for the amino-terminal Met and the subsequent 7 residues of beta-galactosidase so that a hybrid protein is produced; pIN vectors (Van Heeke & Schuster J. Biol. Chem. 264:5503-5509, (1989)); pET vectors (Novagen, Madison Wis.); and the like.

In the yeast Saccharomyces cerevisiae a number of vectors containing constitutive or inducible promoters such as alpha factor, alcohol oxidase and PGH may be used. For reviews, see Ausubel et al. (supra) and Grant et al., (Methods in Enzymology 153:516-544, (1987)).

In cases where plant expression vectors are used, the expression of a sequence encoding variant products may be driven by any of a number of promoters. For example, viral promoters such as the $^{35}$S and 19S promoters of CaMV (Brisson et al., Nature 310:511-514. (1984)) may be used alone or in combination with the omega leader sequence from TMV (Takamatsu et al., EMBO J., 6:307-311, (1987)). Alternatively, plant promoters such as the small subunit of RUBISCO (Coruzzi et al., EMBO J. 3:1671-1680, (1984); Broglie et al., Science 224:838-843, (1984)); or heat shock promoters (Winter J and Sinibaldi R. M., Results Probl. Cell Differ., 17:85-105, (1991)) may be used. These constructs can be introduced into plant cells by direct DNA transformation or pathogen-mediated transfection. For reviews of such techniques, see Hobbs S. or Murry L. E. (1992) in McGraw Hill Yearbook of Science and Technology, McGraw Hill, New York, N.Y., pp 191-196; or Weissbach and Weissbach (1988) Methods for Plant Molecular Biology, Academic Press, New York, N.Y., pp 421-463.

CD40R variants products may also be expressed in an insect system. In one such system, Autographa californica nuclear polyhedrosis virus (AcNPV) is used as a vector to express foreign genes in Spodoptera frugiperda cells or in Trichoplusia larvae. The CD40R variants products coding sequence may be cloned into a nonessential region of the virus, such as the polyhedrin gene, and placed under control of the polyhedrin promoter. Successful insertion of CD40R variants coding sequences will render the polyhedrin gene inactive and produce recombinant virus lacking coat protein coat. The recombinant viruses are then used to infect S. frugiperda cells or Trichoplusia larvae in which variant protein is expressed (Smith et al., J. Virol. 46:584, (1983); Engelhard, E. K. et al., Proc. Nat. Acad. Sci. 91:3224-7, (1994)).

In mammalian host cells, a number of viral-based expression systems may be utilized. In cases where an adenovirus is used as an expression vector, 5 CD40R variants products coding sequences may be ligated into an adenovirus transcription/translation complex consisting of the late promoter and tripartite leader sequence. Insertion in a nonessential E1 or E3 region of the viral genome will result in a viable virus capable of expressing variant protein in infected host cells (Logan and Shenk, Proc. Natl. Acad. Sci. 81:3655-59, (1984). In addition, transcription enhancers, such as the Rous sarcoma virus (RSV) enhancer, may be used to increase expression in mammalian host cells.

Specific initiation signals may also be required for efficient translation of variants products coding sequences. These signals include the ATG initiation codon and adjacent sequences. In cases where CD40R variants products coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf, D. et al., (1994) Results Probl. Cell Differ., 20:125-62, (1994); Bittner et al., Methods in Enzymol 153:516-544, (1987)).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, 1. (1986) Basic Methods in Molecular Biology). Cell-free translation systems can also be employed to produce polypeptides using RNAs derived from the DNA constructs of the present invention.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre-pro" form of the protein may also be important for correct insertion, folding and/or function. Different host cells such as CHO, HeLa, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express variant products may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M., et al., Cell 11:223-32, (1977)) and adenine phosphoribosyltransferase (Lowy I., et al., Cell 22:817-23, (1980)) genes which can be employed in tk- or aprt-cells, respectively. Also, antimetabolite, antibiotic or herbicide resistance can be used as the basis for selection; for example, dhfr which confers resistance to methotrexate (Wigler M., et al., Proc. Natl. Acaci. Sci. 77:3567-70, (1980)); npt, which confers resistance to the aminoglycosides neomycin and G418 (Colbere-Garapin, F. et al., J. Mol. Biol., 150:1-14, (1981)) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan, Proc. Natl. Acad. Sci. 85:8047-51, (1988)). The use of visible markers has gained popularity with such markers as anthocyanins, beta-glucuronidase and its substrate, GUS, and luciferase and its substrates, luciferin and ATP, being widely used not only to identify transformants, but also to quantify the amount of transient or stable protein expression attributable to a specific vector system (Rhodes, C. A. et. al., Methods Mol. Biol., 55:121-131, (1995)).

Host cells transformed with nucleotide sequences encoding CD40R variants products may be cultured under conditions suitable for the expression and recovery of the encoded protein from cell culture. The product produced by a recombinant cell may be secreted or contained intracellularly depending on the sequence and/or the vector used. As will be understood by those of skill in the art, expression vectors containing nucleic acid sequences encoding CD40R variants products can be designed with signal sequences which direct secretion of CD40R variants products through a prokaryotic or eukaryotic cell membrane.

The CD40R variants products may also be expressed as recombinant proteins with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a protease-cleavable polypeptide linker sequence between the purification domain and CD40R variants products is useful to facilitate purification. One such expression vector provides for expression of a fusion protein compromising a variant polypeptide fused to a polyhistidine region separated by an enterokinase cleavage site. The histidine residues facilitate purification on IMIAC (immobilized metal ion affinity chromatography, as described in Porath, et al., Protein Expression and Purification, 3:263-281, (1992)) while the enterokinase cleavage site provides a means for isolating variant polypeptide from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

The CD40R variants products can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. Finally, high performance liquid chromatography (HPLC) can be employed for final purification steps.

C. Use of Varient to Produce Proteins

C.1 Separation:

Sf-9 cells were infected with sCD40 (soluble CD40) expressing baculovirus (Ac-sCD40) comprising the nucleic acid sequence of SEQ ID NO:3 at MOI of 2. The cells were grown in 28° C. at Continuous shaking (90 rpm). At 60 hours post infection (hpi) the medium was collected and cells were separated from the medium by centrifugation at 5000 RPM for 5 minutes. 10 ml medium was separated using cation exchange chromatography with SP-Sepharose column. The Column was equilibrated with PBS pH-6.5 and following loading of the sample on the column the column was washed with PBS to elute the unbound proteins (flow through fraction). Elution was done with increasing concentration of NaCl at flow rate of 2 ml/min (5% NaCl/min).

The different fractions were subjected to SDS-PAGE electrophoresis and to western blotting using anti mCD40 antibody, and the results are shown in FIG. 2.

C. 1 Secretion:

Sf-9 cells were infected with sCD40 expressing baculovirus (Ac-sCD40) at MOI of 2. The cells were grown at 28° C. at continuous shaking (90 rpm) and 1 ml samples were collected at 24, 48 and 60 hours post infection (hpi). Following centrifugation Cells pellet was lysed with lysis buffer (50 mM Tris pH 7.5, 1% triton X100, and protease inhibitor cocktail) at 4° C. for 30 min and sonicated for 30 seconds. The sample was centrifuged for 10 minutes at 14000 rmp and the sup was designated Pellet. 40 µl of the pellet preparation and of the medium (Designated Medium) were supplemented with sample buffer and electrophoreses on a 15° SDS-PAGE. Following electrophoresis the gel was subjected to a semi dry protein transfer onto a nitrocellulose membrane. The protein. Finally, high performance liquid chromatography (HPLC) can be employed for final purification steps.

C. Use of Varient to Produce Proteins

C.1 Separation:

Sf-9 cells were infected with sCD40 (soluble CD40) expressing baculovirus (Ac-sCD40) comprising the nucleic acid sequence of SEQ ID NO:3 at MOI of 2. The cells were grown in 28° C. at continuous shaking (90 rpm). At 60 hours post infection (hpi) the medium was collected and cells were separated from the medium by centrifugation at 5000 RPM for 5 minutes. 10 ml medium was separated using cation exchange chromatography with SP-Sepharose column. The Column was equilibrated with PBS pH-6.5 and following loading of the sample on the column the column was washed with PBS to elute the unbound proteins (flow through fraction). Elution was done with increasing concentration of NaCl at flow rate of 2 ml/min (5% NaCl/min).

The different fractions were subjected to SDS-PAGE electrophoresis and to western blotting using anti mCD40 antibody, and the results are shown in FIG. 2.

C.1 Secretion:

Sf-9 cells were infected with sCD40 expressing baculovirus (Ac-sCD40) at MOI of 2. The cells were grown at 28° C. at continuous shaking (90 rpm) and 1 ml samples were collected at 24, 48 and 60 hours post infection (hpi). Following centrifugation Cells pellet was lysed with lysis buffer (50 mM Tris pH 7.5, 1% triton X100, and protease inhibitor cocktail) at 4° C. for 30 min and sonicated for 30 seconds. The sample was centrifuged for 10 minutes at 14000 rmp and the sup was designated Pellet. 40 µl of the pellet preparation and of the medium (Designated Medium) were supplemented with sample buffer and electrophoreses on a 15% SDS-PAGE. Following electrophoresis the gel was subjected to a semi dry protein transfer onto a nitrocellulose membrane. The membrane was incubated with anti mCD40 antibody for 2 hours and with secondary anti rabbit antibody for an additional 1 hour.

Figure 3:
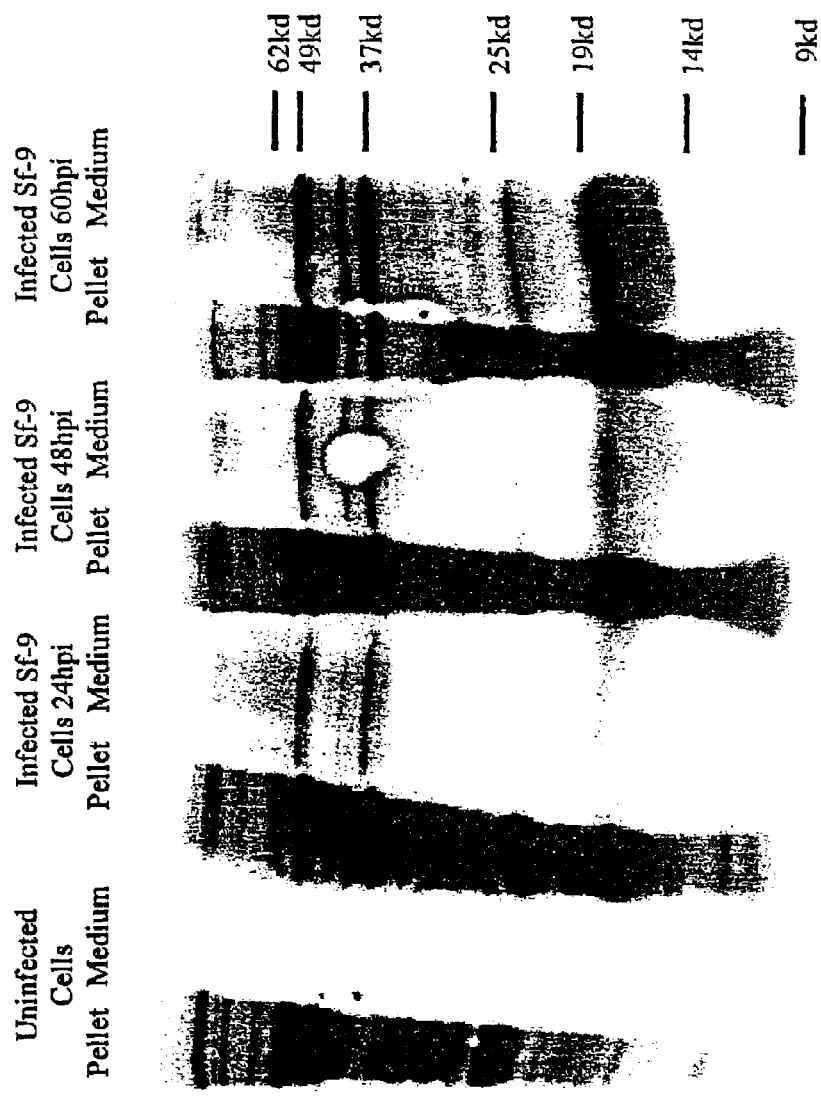
FIG. 3 shows Western blot analysis of CD40 secreted from St-0 cells transfected with an expression vector.

Detection of the signal was done using a commercial western blot detection kit, and the results are shown in FIG. 3.

D. Diagnostic Applications Utilizing Nucleic Acid Sequences

The nucleic acid sequences of the present invention may be used for a variety of diagnostic purposes. The nucleic acid sequences may be used to detect and quantitate expression of the CD40R variant in patient's cells, e.g. biopsied lo tissues, by detecting the presence of mRNA coding for the CD40R variants products. Alternatively, the assay may be used to detect the soluble variants in the serum or blood. This assay typically involves obtaining total mRNA from the tissue or serum and contacting the mRNA with a nucleic acid probe. The probe is a nucleic acid molecule of at least 20 nucleotides, preferably 20-30 nucleotides, capable of specifically hybridizing with a sequence included within the sequence of a nucleic acid molecule encoding the CD40R variant product under hybridizing conditions, detecting the presence of mRNA hybridized to the probe, and thereby detecting the expression of variant. This assay can be used to distinguish between absence, presence, and excess expression of CD40R variants products and to monitor levels of CD40R variants expression during therapeutic intervention. In addition, the assay may be used to compare the levels of the CD40R variant of the invention to the levels of the original CD40R sequence from which it has been varied or to levels of each other, which comparison may have some physiological meaning.

The invention also contemplates the use of the nucleic acid sequences as a diagnostic for diseases resulting from inherited defective variants sequences, or diseases in which the ratio of the amount of the original CD40R sequence from which the CD40R variants were varied to the novel CD40R variants of the invention is altered. These sequences can be detected by comparing the sequences of the defective (i.e., mutant) CD40R variants coding region with that of a normal coding region. Association of the sequence coding for mutant CD40R variants products with abnormal variants products activity may be verified. In addition, sequences encoding mutant CD40R variants products can be inserted into a suitable vector for expression in a functional assay system (e.g., colorimetric assay, complementation experiments in a variant protein deficient strain of HEK2993 cells) as yet another means to verify or identify mutations. Once mutant genes have been identified, one can then screen populations of interest for carriers of the mutant gene.

Individuals carrying mutations in the nucleic acid sequences of the present invention may be detected at the DNA level by a variety of techniques. Nucleic acids used for diagnosis may be obtained from a patients cells, including but not limited to such as from blood, urine, saliva, placenta, tissue biopsy and autopsy material. Genomic DNA may be used directly for detection or may be amplified enzymatically by using PCR (Saiki, et al., *Nature* 324:163-166, (1986)) prior to analysis. RNA or cDNA may also be used for the same purpose. As an example, PCR primers complementary to the nucleic acid of the present invention can be used to identify and analyze mutations in the gene of the present invention. Deletions and insertions can be detected by a change in size of the amplified product in comparison to the normal genotype.

Point mutations can be identified by hybridizing amplified DNA to radiolabeled RNA of the invention or alternatively, radiolabeled antisense DNA sequences of the invention. Sequence changes at specific locations may also be revealed by nuclease protection assays, such RNase and S1 protection or the chemical cleavage method (e.g. Cotton, el al *Proc. Natl Acad. Sci. USA,* 85:4397-4401, (1985)), or by differences in melting temperatures. "Molecular beacons" (Kostrikis L. G. et al., Science 279:1228-1229, (1998)), hairpin-shaped, single-stranded synthetic oligo-nucleotides containing probe sequences which are complementary to the nucleic acid of the present invention, may also be used to detect point mutations or other sequence changes as well as monitor expression levels of variant product. Such diagnostics would be particularly useful for prenatal testing.

Another method for detecting mutations uses two DNA probes which are designed to hybridize to adjacent regions of a target, with abutting bases, where the region of known or suspected mutation(s) is at or near the abutting bases. The two probes may be joined at the abutting bases, e.g., in the presence of a ligase enzyme, but only if both probes are correctly base paired in the region of probe junction. The presence or absence of mutations is then detectable by the presence or absence of ligated probe.

Also suitable for detecting mutations in the CD40R variants products coding sequences are oligonucleotide array methods based on sequencing by hybridization (SBH), as described, for example, in U.S. Pat. No. 5,547,839. In a typical method, the DNA target analyte is hybridized with an array of oligonucleotides formed on a microchip. The sequence of the target can then be "read" from the pattern of target binding to the array.

E. Therapeutic Applications of Nucleic Acid Sequences

Nucleic acid sequences of the invention may also be used for therapeutic purposes. Turning first to the second aspect of the invention (i.e. inhibition of expression of CD40R variants), expression of CD40R variants products may be modulated through antisense technology, which controls gene expression through hybridization of complementary nucleic acid sequences, i.e. antisense DNA or RNA, to the control, 5' or regulatory regions of the gene encoding variant product. For example, the 5' coding portion of the nucleic acid sequence sequence which codes for the product of the present invention is used to design an antisense oligonucleotide of from about 10 to 40 base pairs in length. Oligonucleotides derived from the transcription start site, e.g. between positions −10 and +10 from the start site, are preferred. An antisense DNA oligonucleotide is designed to be complementary to a region of the nucleic acid sequence involved in transcription (Lee et al., Nucl. Acids, Res., 6:3073, (1979); Cooney et al. Science 241:456, (1988); and Dervan et al., Science 251:1360, (1991)), thereby preventing transcription and the production of the variant products. An antisense RNA oligonucleotide hybridizes to the mRNA in vivo and blocks translation of the mRNA molecule into the variant products (Okano J. Neurochem. 56:560, (1991)). The antisense constructs can be delivered to cells by procedures known in the art such that the antisense RNA or DNA may be expressed in vivo. The antisense may be antisense mRNA or DNA sequence capable of coding such antisense mRNA. The antisense mRNA or the DNA coding thereof can be complementary to the full sequence of nucleic acid sequences coding for the CD40R variant protein or to a fragment of such a sequence which is sufficient to inhibit production of a protein product. Antisense technologies can also be used for inhibiting expression of one variant as compared to the other, or inhibiting the expression of the variant/s as compared to the original sequence.

Turning now to the first aspect of the invention, i.e. expression of CD40R variants, expression of CD40R variants products may be increased by providing coding sequences for coding for said CD40R variants products under the control of suitable control elements ending its expression in the desired host.

The nucleic acid sequences of the invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The products of the invention may also be employed in accordance with the present invention by expression of such polypeptides in vivo, which is often referred to as "gene therapy." Cells from a patient may be engineered with a nucleic acid sequence (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by procedures known in the art. As known in the art, a producer cell for producing a retroviral particle containing RNA encoding the polypeptides of the present invention may be administered to a patient for engineering cells in vivo and expression of the polypeptide in vivo. These and other methods for administering products of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, psi-2, psi-AM, PA12, T19-14X, VT-19-17-H2, psi-CRE, psi-CRIP, GP+E-86, GP+envAm12, and DAN cell lines as described in Miller (Human Gene Therapy, Vol. 1, pg. 5-14, (1990)). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The genes introduced into cells may be placed under the control of inducible promoters, such as the radiation-inducible Egr-1 promoter, (Maceri, H. J., et al., Cancer Res., 56(19):4311 (1996)), to stimulate variant production or antisense inhibition in response to radiation, eg., radiation therapy for treating tumors.

EXAMPLE II

CD40R Variants Products

The substantially purified CD40R variant product of the invention has been defined above as the product coded from the nucleic acid sequence of the invention. Preferably the amino acid sequence is an amino acid sequence having at least 90% identity the sequence identified as SEQ ID NO:7 to SEQ ID NO:12. The protein or polypeptide may be in mature and/or modified form, also as defined above, for example, modified by cleavage of the leader sequence. Also contemplated are protein fragments having at least 10 contiguous amino acid residues, preferably at least 10-20 residues, derived from the CD40R variant products, as well as homologues as explained above.

The sequence variations are preferably those that are considered conserved substitutions, as defined above. Thus, for example, a protein with a sequence having at least 90% sequence identity with the products identified as SEQ ID NO:7 to SEQ ID NO:12, preferably by utilizing conserved substitutions as defined above is also part of the invention, and provided that it is not identical to the original peptide from which it has been varied (typically the substitutions are in regions where the variant differs from the original sequence as for example in Table 1). In a more specific embodiment, the protein has or contains the sequence identified SEQ ID NO:7 to SEQ ID NO:12. The CD40R variants products may be (i) one in which one or more of the amino acid residues in a sequence listed above are substituted with a conserved or non-conserved amino acid residue (preferably a conserved amino acid residue), or (ii) one in which one or more of the amino acid residues includes a substituent group, or (iii) one in which the CD40R variants products is fused with another compound, such as a compound to increase the half-life of the protein (for example, polyethylene glycol (PEG)), or a moiety which serves as targeting means to direct the protein to its target tissue or target cell population (such as an antibody), or (iv) one in which additional amino acids are fused to the CD40R variant product. Such fragments, variants and derivatives are deemed to be within the scope of those skilled in the art from the teachings herein.

A. Preparation of CD40R Variants Products

Recombinant methods for producing and isolating the CD40R variant products, and fragments of the protein are described above.

In addition to recombinant production, fragments and portions of variant products may be produced by direct peptide synthesis using solid-phase techniques (cf. Stewart et al., (1969) Solid-Phase Peptide Synthesis, WH Freeman Co, San Francisco; Merrifield J., *J. Am. Chem. Soc.*, 85:2149-2154, (1963)). In vitro peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Fragments of CD40R variants products may be chemically synthesized separately and combined using chemical methods to produce the full length molecule.

B. Therapeutic uses and Compositions Utilizing the CD40R Variants Products

The CD40R variants products of the invention are generally useful in treating diseases and disorders which can be cured or ameliorated by lowering the level of any of the CD40 ligands. Examples of such diseases are various autoimmune diseases as well as GVHD.

CD40R variant products or fragments may be administered by any of a number of routes and methods designed to provide a consistent and predictable concentration of compound at the target organ or tissue. The product-containing compositions may be administered alone or in combination with other agents, such as stabilizing compounds, and/or in combination with other pharmaceutical agents such as drugs or hormones.

CD40R variants product-containing compositions may be administered by a number of routes including, but not limited to oral, intravenous, intramuscular, transdermal, subcutaneous, topical, sublingual, or rectal means as well as by nasal application. CD40R variant product-containing compositions may also be administered via liposomes. Such administration routes and appropriate formulations are generally known to those of skill in the art.

The CD40R variants products can be given via intravenous or intraperitoneal injection. Similarly, the product may be injected to other localized regions of the body. The product may also be administered via nasal insufflation. Enteral administration is also possible. For such administration, the product should be formulated into an appropriate capsule or elixir for oral administration, or into a suppository for rectal administration.

The foregoing exemplary administration modes will likely require that the product be formulated into an appropriate carrier, including ointments, gels, suppositories. Appropriate formulations are well known to persons skilled in the art.

Dosage of the product will vary, depending upon the potency and therapeutic index of the particular polypeptide selected.

A therapeutic composition for use in the treatment method can include the product in a sterile injectable solution, the polypeptide in an oral delivery vehicle, the product in an aerosol suitable for nasal administration, or the product in a nebulized form, all prepared according to well known methods. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The product of the invention may also be used to modulate endothelial differentiation and proliferation as well as to modulate apoptosis either ex vivo or in vitro, for example, in cell cultures.

EXAMPLE III

Anti-Variant Antibodies

A. Synthesis

In still another aspect of the invention, the purified variants products are used to produce anti-variant antibodies which have diagnostic and therapeutic uses related to the activity, distribution, and expression of the CD40R variants products.

Antibodies to the CD40R variant may be generated by methods well known in the art. Such antibodies may include, but are not limited to, polyclonal, monoclonal, chimeric, humanized, single chain, Fab fragments and fragments produced by an Fab expression library. Antibodies, i.e., those which inhibit dimer formation, are especially preferred for therapeutic use.

A fragment of the CD40R variants products for antibody induction is not required to feature biological activity but has to feature immunological activity; however, the protein fragment or oligopeptide must be antigenic. Peptides used to induce specific antibodies may have an amino acid sequence consisting of at least five amino acids, preferably at least 10 amino acids of the sequences specified in SEQ ID NO:7 to SEQ ID NO:12. Preferably they should mimic a portion of the amino acid sequence of the natural protein and may contain the entire amino acid sequence of a small, naturally occurring molecule. Short stretches of CD40R variants proteins amino acids may be fused with those of another protein such as keyhole limpet hemocyanin and antibody produced against the chimeric molecule. Procedures well known in the art can be used for the production of antibodies to CD40R variants products.

For the production of antibodies, various hosts including goats, rabbits, rats, mice, etc may be immunized by injection with CD40R variants products or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Monoclonal antibodies to CD40R variants protein may be prepared using any technique which provides for the production of antibody molecules by continuous cell lines in culture. These include but are not limited to the hybridoma technique originally described by Koehler and Milstein (*Nature* 256:495-497, (1975)), the human B-cell hybridoma technique (Kosbor et al., *Immunol. Today* 4:72, (1983); Cote et al., *Proc. Natl. Acad. Sci.* 80:2026-2030, (1983)) and the EBV-hybridoma technique (Cole, et al., *Mol. Cell Biol.* 62:109-120, (1984)).

Techniques developed for the production of "chimeric antibodies", the splicing of mouse antibody genes to human antibody genes to obtain a molecule with appropriate antigen specificity and biological activity can also be used (Morrison et al., *Proc. Natl. Acad. Sci.* 81:6851-6855, (1984); Neuberger et al., *Nature* 312:604-608, (1984); Takeda et al., *Nature* 314:452454, (1985)). Alternatively, techniques described for the production of single chain antibodies (U.S. Pat. No. 4,946,778) can be adapted to produce single-chain antibodies specific for the variant protein.

Antibodies may also be produced by inducing in vivo production in the lymphocyte population or by screening recombinant immunoglobulin libraries or panels of highly specific binding reagents as disclosed in Orlandi et al. (*Proc. Natl. Acad. Sci.* 86:3833-3837, 1989)), and Winter G and Milstein C., (*Nature* 349:293-299, (1991)).

Antibody fragments which contain specific binding sites for the CD40R variant protein may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W. D. et al., *Science* 256:1275-1281, (1989)).

B. Diagnostic Applications of Antibodies

A variety of protocols for competitive binding or immunoradiometric assays using either polyclonal or monoclonal antibodies with established specificities are well known in the art. Such immunoassays typically involve the formation of complexes between the CD40R variants products and its specific antibody and the measurement of complex formation. A two-site, monoclonal-based immunoassay utilizing monoclonal antibodies reactive to two noninterfering epitopes on a specific variant product is preferred, but a competitive binding assay may also be employed. These assays are described in Maddox D. E., et al., (*J. Exp. Med.* 158:1211, (1983)).

Antibodies which specifically bind the CD40R variant product are useful for the diagnosis of conditions or diseases characterized by expression of the novel CD40R variants of the invention (where normally it is not expressed) by over or under expression of CD40R variants as well as for detection of diseases in which the proportion between the amount of the CD40R variants of the invention and the original CD40R sequence from which it varied is altered. Alternatively, such antibodies may be used in assays to monitor patients being treated with CD40R variants products. Diagnostic assays for variants proteins include methods utilizing the antibody and a label to detect variants products in human body fluids or extracts of cells or tissues. The products and antibodies of the present invention may be used with or without modification. Frequently, the proteins and antibodies will be labeled by joining them, either covalently or noncovalently, with a reporter molecule A wide variety of reporter molecules are known in the art.

A variety of protocols for measuring the CD40R variants products, using either polyclonal or monoclonal antibodies specific for the respective protein are known in the art. Examples include enzyme-lied immunosorbent assay (ELISA), radioimmunoassay (RIA), and fluorescent activated cell sorting (FACS). As noted above, a two-site, monoclonal-based immunoassay utilizing monoclonal antibodies reactive to two non-interfering epitopes on CD40R variants products is preferred, but a competitive binding assay may be employed. These assays are described, among other places, in Maddox, et al. (supra). Such protocols provide a basis for diagnosing altered or abnormal levels of CD40R variants products expression. Normal or standard values for CD40R variants products expression are established by combining body fluids or cell extracts taken from normal subjects, preferably human, with antibodies to CD40R variants products under conditions suitable for complex formation which are well known in the art. The amount of standard complex formation may be quantified by various methods, preferably by photometric methods. Then, standard values obtained from normal samples may be compared with values obtained from samples from subjects potentially affected by disease. Deviation between standard and subject values establishes the presence of disease state.

The antibody assays are useful to determine the level of CD40R variants products present in a body fluid sample, in order to determine whether it is being expressed at all, whether it is being overexpressed or underexpressed in the tissue, or as an indication of how CD40R variants levels of variable products are responding to drug treatment.

C. Therapeutic Uses of Antibodies

In addition to their diagnostic use the antibodies may have a therapeutical utility in blocking or decreasing the activity of the CD40R variant product in pathological conditions where beneficial effect can be achieved by such a decrease.

The antibody employed is preferably a humanized monoclonal antibody, or a human Mab produced by known globulin-gene library methods. The antibody is administered typically as a sterile solution by IV injection, although other parenteral routes may be suitable. Typically, the antibody is administered in an amount between about 1-15 mg/kg body weight of the subject. Treatment is continued, e.g., with dosing every 1-7 days, until a therapeutic improvement is seen.

Although the invention has been described with reference to specific methods and embodiments, it is appreciated that various modifications and changes may be made without departing from the invention.

What is claimed is:

1. An isolated polypeptide comprising the amino acid sequence set forth in SEQ ID NO: 7.

2. A pharmaceutical composition comprising the polypeptide of claim 1 and a pharmaceutically acceptable carrier.

* * * * *

UNITED STATES PATENT AND TRADEMARK OFFICE
CERTIFICATE OF CORRECTION

PATENT NO. : 6,994,994 B1
DATED : February 7, 2006
INVENTOR(S) : Savitzky et al.

It is certified that error appears in the above-identified patent and that said Letters Patent is hereby corrected as shown below:

<u>Title page,</u>
Item [73], Assignee, change to -- Compugen LTD --.

Signed and Sealed this

Twenty-third Day of May, 2006

JON W. DUDAS
*Director of the United States Patent and Trademark Office*